United States Patent [19]

Aisenberg et al.

[11] 4,005,701
[45] Feb. 1, 1977

[54] NOISE REJECTING ELECTRONIC SPHYGMOMANOMETER AND METHODS FOR MEASURING BLOOD PRESSURE

[75] Inventors: Sol Aisenberg, Natick; Ronald W. Chabot, Winchester, both of Mass.

[73] Assignee: Whittaker Corporation, Los Angeles, Calif.

[22] Filed: June 11, 1975

[21] Appl. No.: 585,889

[52] U.S. Cl. .................. 128/2.05 G; 128/2.05 A; 128/2.05 M; 128/2.05 S
[51] Int. Cl.² .......................................... A61B 5/02
[58] Field of Search ............... 128/2.05 A, 2.05 G, 128/2.05 M, 2.05 S, 2.05 E

[56] References Cited

UNITED STATES PATENTS

| | | | |
|---|---|---|---|
| 2,827,040 | 3/1958 | Gilford | 128/2.05 A |
| 3,157,177 | 11/1964 | Smith | 128/2.05 A |
| 3,533,401 | 10/1970 | Streu | 128/2.05 A |
| 3,633,568 | 1/1972 | Hobel | 128/2.05 M |
| 3,771,515 | 11/1973 | Hurwitz | 128/2.05 G |
| 3,880,145 | 4/1975 | Blick | 128/2.05 A |
| 3,905,354 | 9/1975 | Lichowsky | 128/2.05 M |

FOREIGN PATENTS OR APPLICATIONS

| | | | |
|---|---|---|---|
| 1,258,016 | 1/1968 | Germany | 128/2.05 E |

*Primary Examiner*—Kyle L. Howell
*Attorney, Agent, or Firm*—Henry M. Bissell

[57] ABSTRACT

A noise rejecting electronic sphygmomanometer comprises a conventional cuff-type sphygmomanometer having an inflatable bladder and pressure monitoring manometer connected thereto. A first microphone, having a sound pickup directed inwardly to be toward a patient's arm when the cuff is installed thereabout, is provided for picking up Korotkoff sounds as the cuff is deflated and blood flow in a patient's arm resumes. To avoid spurious indications caused by background sounds, a second microphone, having a pickup directed to pickup background noises, is also provided within the cuff. The outputs of both microphones are fed into electronic discrimination circuitry.

29 Claims, 9 Drawing Figures

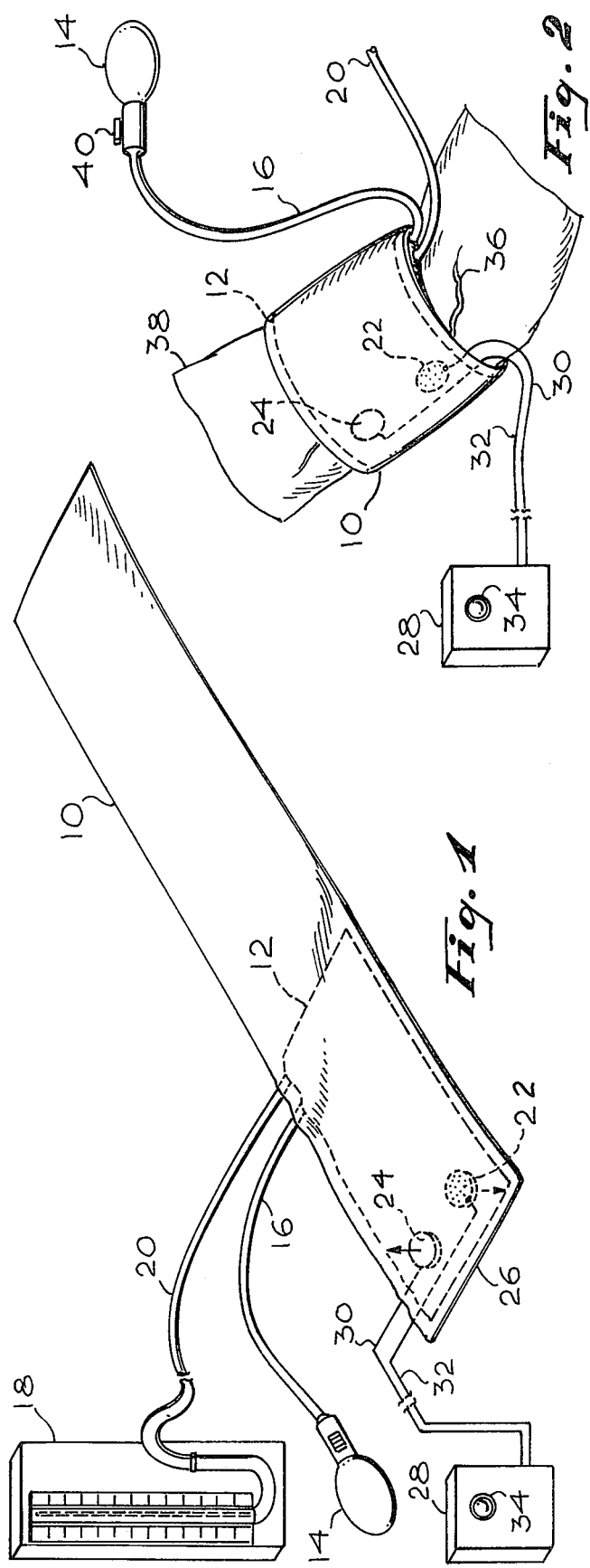
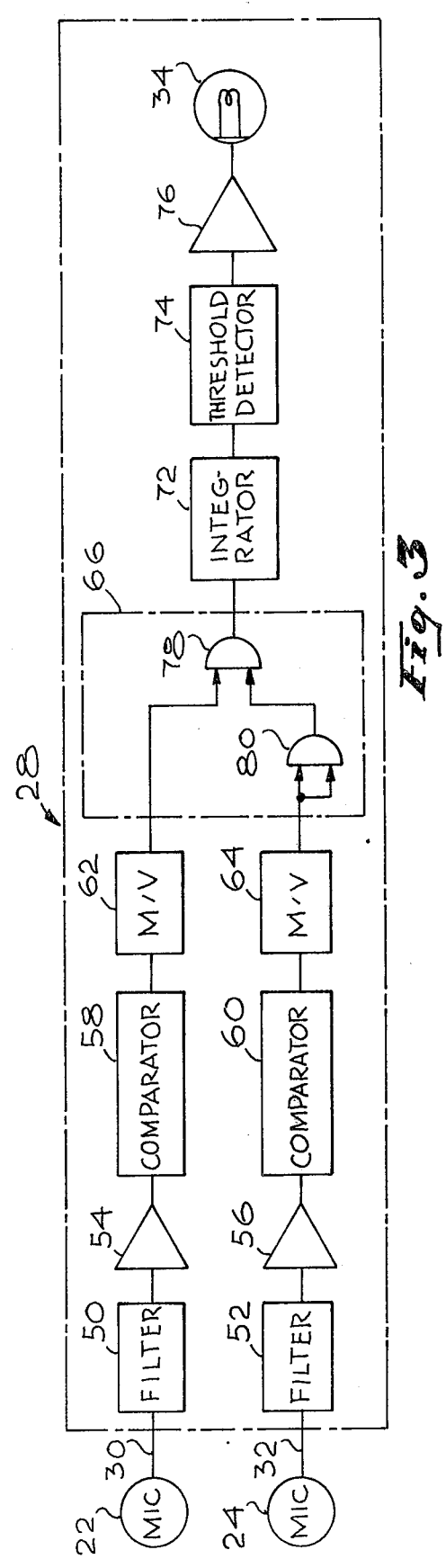

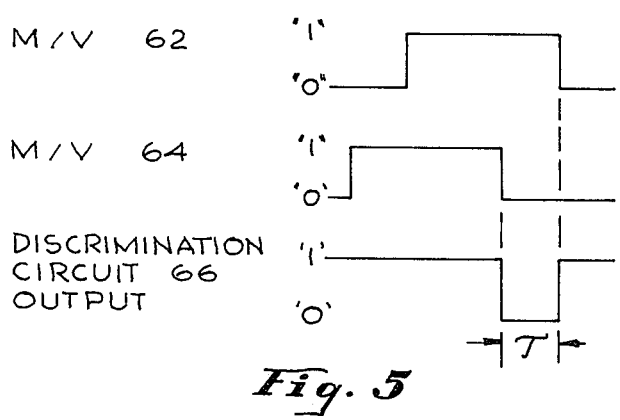
Fig. 4
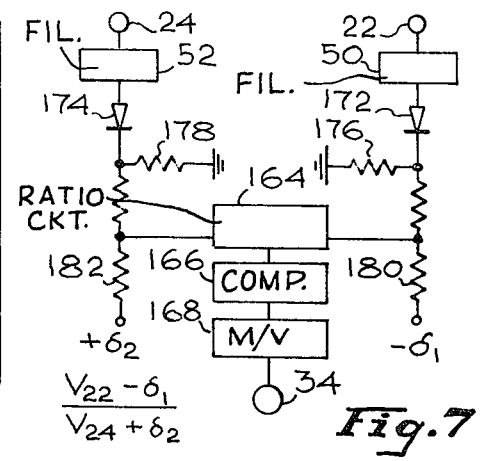
Fig. 7
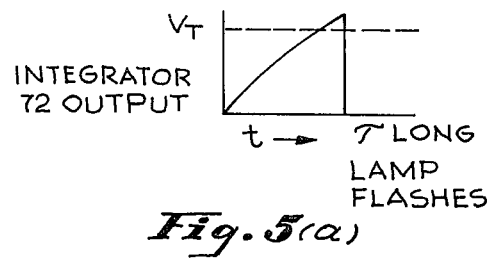
Fig. 5
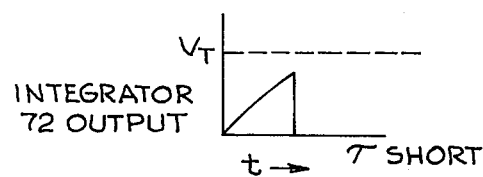
Fig. 5(a)
Fig. 5(b)
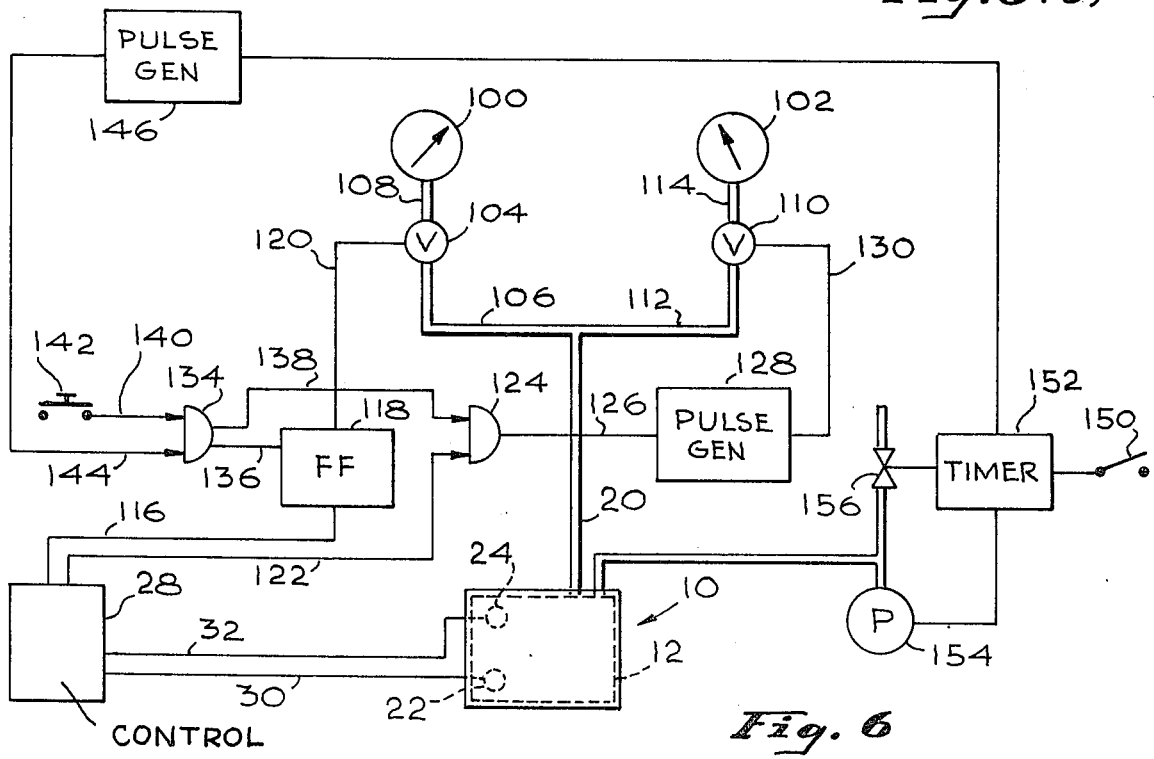
Fig. 6

NOISE REJECTING ELECTRONIC SPHYGMOMANOMETER AND METHODS FOR MEASURING BLOOD PRESSURE

BACKGROUND OF THE INVENTION

1. Field of the Invention

The present invention relates to the field of blood pressure measuring instruments or sphygmomanometers; more particularly, it relates to such instruments utilizing acoustical pickups or microphones for determining, by blood sounds, the pressure levels at which systolic and diastolic blood pressure are to be measured.

2. Description of the Prior Art

Periodic and accurate blood pressure determinations are essential to proper diagnosis of heart function, and particularly, to discover hypertension in humans. Instruments used to measure blood pressure are called sphygmomanometers, the most common type of such instruments being an inflatable cuff which is secured around a patient's upper arm. The operator listens, normally via a stethoscope positioned against the patient's artery in the lower arm, to the heartbeat and inflates the cuff until the heartbeat no longer can be heard. Blood flow is then effectively cut off to the lower arm. The pressure in the cuff is at all times registered on a pressure gauge, generally a mercury manometer. When the blood flow to the lower arm is completely occluded, pressure is slowly released from the cuff. The cuff pressure at which the operator again just begins to hear characteristic blood flow noises (Korotkoff sounds) is termed the systolic blood pressure of the patient. Additional pressure is released from the cuff until the Korotkoff sounds momentarily get louder and then fade. The point at which the Korotkoff sounds first disappear is termed the diastolic blood pressure.

The described method requires relatively subjective determination of sound levels by the operator. Various extraneous factors, such as ambient noise and the operator's hearing, may affect the determination of exactly when the Korotkoff sounds can first be heard as the cuff is deflated and exactly when they later disappear. As accurate and repeatable blood pressure determinations may be essential to a proper determination of the patient's well being, improved and less subjective methods for determining blood pressure are desirable.

In order to eliminate subjective sound determinations by a stethoscope, cuff-type sphygmomanometers have sometimes been modified by insertion of a microphone in the cuff, the microphone being positioned over a restricted brachial artery when the cuff is fastened about a patient's arm. The microphone, which replaces the stethoscope, is electronically connected to an indicator, for example a light, and the cuff is inflated as above described until the blood supply is cut off to the patient's lower arm; then pressure is slowly released from the cuff. As the systolic pressure, when blood flow just resumes, the microphone detects the Korotkoff sounds and causes the light (or other indicator) to be actuated. As the cuff is further deflated, the Korotkoff sound is picked up at each pulse beat and, in typical systems, a light flashes at each beat. When diastolic pressure is reached, there is no longer a restriction of the blood vessels, and consequently no further Korotkoff sounds are picked up. At this point, flashing of the light stops. Systolic blood pressure is read from the manometer when the light first starts flashing, and the diastolic pressure is read when the light stops flashing.

A principal difficulty with the use of a microphone to pick up blood sounds is that background or extraneous noises arising, for example, from movement of the patient's arm or from the surrounding environment are also picked up by the microphone. Erroneous indications, and hence erroneous blood pressure readings, thus often occur.

Gilford, U.S. Pat. No. 2,827,040, discloses apparatus wherein blood sounds picked up by a microphone are correlated with blood pressure pulses caused by the heartbeat. An indicator is to be actuated only when picked-up sounds occur simultaneously with pressure pulses. This is intended to screen out extraneous noise sources. If, however, a background noise is picked up coincidentally with a pulse beat an erroneous indication will be given. Further improvement over such a system is needed.

SUMMARY OF THE INVENTION

A noise rejecting electronic sphygmomanometer, in accordance with the invention, comprises a flexible cuff, adapted for fastening around a patient's limb, together with an inflatable bladder installed therein and means for monitoring pressure in the bladder. A first, blood-sound acoustical pickup and a second, noise acoustical pickup are installed in the cuff, the first pickup having a sound receiving portion being directed inwardly to be over a brachial artery to pick up Korotkoff sounds when the cuff is installed. The sound receiving portion of the second acoustical pickup is directed to pick up background noises, but not blood sound noises. Discriminating means are connected to the pickups for comparing electrical signals received therefrom. An output is caused to be at a first predetermined level when and only when there is strong assurance that the sounds picked up by the first pickup are Korotkoff sounds and not background noises, and is at a second level for all other sound conditions.

More particularly, an indicator is connected to the discriminating means output and is caused to give an indication only when the discriminating means output is at the first level; that is, when Korotkoff blood sounds are being picked up by the first microphone. In this manner, as pressure is released from the cuff bladder, an operator records, from a manometer, systolic blood pressure at the onset of the indications and records diastolic blood pressure at the cessation of the indications.

The discriminating means includes means for filtering out electrical signals from the two pickups, which may be microphones, other than those in a band for example about 5 Hz wide and centered about 90 Hz, a frequency representative of strong turn-on and turn-off blood sounds and not representative of common background noises. Within the discriminating means, the filtered signals are digitized and shaped into square waves which are fed into a discrimination circuit which compares signals from both microphones. The discriminator output is at the first level when there is a signal from the first microphone and no coincident signal from the second microphone, and is at the second level for all other signal conditions. The output of the discrimination circuit is integrated and then fed into a threshold detector, both of which cooperate to determine if any out-of-coincidence time is sufficiently great to provide an indication of blood sound, such time being predetermined to be about 50 milliseconds.

In a variation, according to one aspect of the invention, two pressure gauges are separately connected to the cuff bladder, the first through a normally open valve and the second through a normally closed valve. Circuitry causes the normally open valve to close, trapping pressure in the first gauge at the onset of the indications and causes the normally closed valve to momentarily open at each indication to admit pressure into the second gauge. When the indications cease, pressure is trapped in the second gauge. Systolic blood pressure is then read from the first gauge and diastolic blood pressure is read from the second gauge.

In another variation, according to a second aspect of the invention, indication is provided only when the ratio between the signal magnitude from the first (blood sound) microphone and that of the second (noise) microphone is greater than a predetermined level. To this end, filtered microphone signals are fed into a ratio circuit which controls operation of the indicator light.

Corresponding methods for measuring a patient's systolic and diastolic blood pressure are thereby provided.

A reliable apparatus and corresponding method for measuring a patient's systolic and diastolic blood pressure are provided which utilize, rather than a conventional stethoscope, a pair of microphones, one of which is directed to pick up blood sounds and the other of which is directed to pick up background noises. By comparing the output signals from both microphones, and rejecting all signals from the blood-sound microphone which may be caused by background noises, an indication is given only when there is a very strong assurance that Korotkoff blood sounds are actually being picked up. An operator is thus assured that the onset of the indications signals the onset of Korotkoff blood noises and that systolic blood pressure should be read at this point. A cessation of the indications informs the operator that the Korotkoff noises have stopped, and at this point the diastolic blood pressure is read. Also, means may be provided for automatically registering systolic and diastolic blood pressure on pressure gauges such that an operator need not watch for indications or make instantaneous readings from a pressure indicator.

BRIEF DESCRIPTION OF THE DRAWING

A better understanding of the present invention may be had from a consideration of the following detailed description, taken in conjunction with the accompanying drawings, in which:

FIG. 1 is a perspective view, showing the sphygmomanometer apparatus of the present invention with the cuff unrolled;

FIG. 2 is a perspective view, showing the sphygmomanometer apparatus with the cuff wrapped and fastened around a patient's arm;

FIG. 3 is a block diagram schematic of the electronic circuitry;

FIG. 4 is a logic diagram of the electronic circuitry;

FIGS. 5, 5a and 5b are waveform diagrams showing gate output vs. multivibrator output for the condition of partially coincident signals from both microphones;

FIG. 6 is a scehematic diagram of a variation of the invention showing connection of the apparatus to a "pneumatic memory"; and FIG. 7 is an electrical schematic of a second variation of the invention, showing an alternative means for microphone signal discrimination.

DESCRIPTION OF THE PREFERRED EMBODIMENT

Referring to FIGS. 1 and 2, the noise rejecting sphygmomanometer, described briefly, comprises a conventional blood pressure cuff 10 having an inflatable bladder 12 positioned at one end thereof, a hand pump 14 connected to the bladder by a tube 16, and a pressure measuring instrument, for example, mercury manometer, 18 connected to the bladder by a tube 20. A first, bloodsound acoustical pickup or microphone 22 and a second noise acoustical pickup or microphone 24, disposed between the bladder 12 and an inner layer of a cuff, preferably along a cuff end edge 26, are connected to an electronic control box 28 by electrical lines 30 and 32 respectively. An indicator light 34 on the box 28, responsive to sounds picked up by the microphones 22 and 24, indicates only the presence of blood flow or Korotkoff sounds picked up by the first microphone, as more particularly described below, thereby enabling an operator to determine when systolic and diastolic blood pressure readings should be read from the instrument 18.

More particularly, the first microphone 22, which replaces the stethoscope conventionally used with a cuff type sphygmomanometer, is positioned having its sound pickup portion directed inwardly so that it may easily pick up blood sounds from a brachial artery 36 over which it is positioned when the cuff 10 is installed around a patient's arm 38 (FIG. 2). When the bladder 12 is inflated and blood flow to the portion of the artery 36 over which the first microphone 22 is positioned is blocked, no blood sounds are picked up. As pressure in the bladder 12 is released, by a valve 40 on the pump 14, blood starts flowing in the artery 36 and the distinctive Korotkoff sounds are picked up by the microphone 22. At the onset of such sounds, a systolic blood pressure is to be measured. When more pressure is released from the bladder 12, the Korotkoff sounds, heard at every heartbeat, diminish as arterial restriction is reduced. Diastolic blood pressure is to be measured at the pressure where the Korotkoff sounds first disappear.

There exists, however, a possibility that extraneous sounds—room noises, patient movements noises, etc.—may be picked up by the microphone 22. If the indicator light 34 were triggered by all sounds picked up by the first microphone 22, erroneous indications, and hence erroneous blood pressure readings, might result. To prevent this, sound discrimination is provided so that the indicator light 34 lights only when there is strong assurance that the sounds picked up by the first microphone 22 are actually Korotkoff sounds. To this end, the second microphone 24 is preferably positioned with its sound pickup portion directed outwardly away from the brachial artery 36 to pick up background noises but not blood flow sounds. However, if the second microphone 24 is not positioned to be over an artery when the cuff 10 is fastened about a patient's arm, the microphone sound pickup portion thereof may alternatively be directed inwardly as is the pickup portion of the microphone 22. To prevent as much extraneous sound pickup as possible, the backs of both microphones 22 and 24 may be sound insulated. Further, the microphones 22 and 24 are remotely located from the bladder connection ends of the tubes 16 and 20, and the electrical lines 30 and 32 are brought out of the cuff remotely from the tubes 16 and 20.

Signal discrimination is provided by electronics within the control box 28 which compare for coincidence electrical impulses received from the first and second microphones 22 and 24, so that only when there is an impulse from the first or bloodsound microphone and no simultaneous impulse from the second or noise microphone—indicating that a true Korotkoff sound has been picked up—is the light 34 triggered.

As depicted schematically in FIG. 3, impulses from each of the microphones 22 and 24 are separately filtered by conventional first and second bandpass filters 50 and 52, respectively, which preferably allow signals within a band width of only about 5 Hz, and centered about 90 Hz, to pass. The 90 Hz level is selected because at this frequency there is a rapid turn-on and turn-off of Korotkoff sounds and muscle noises, which are a common cause of extraneous sounds, are fairly low.

Outputs from the two filters 50 and 52 are separately amplified by conventional amplifiers 54 and 56 respectively. Outputs from these amplifiers 54 and 56 are formed into square waves by conventional comparators 58 and 60. Each series of filter, amplifier and comparator 50, 54 and 58 or 52, 56 and 60 may comprise separate portions of a single integrated circuit, for example a type 3900 quad operational amplifier.

Square waves from the comparators 58 and 60 are separately fed into conventional, astable multivibrators 62 and 64 for conversion into square wave pulses having pulse widths of about 200 milliseconds. The two multivibrators 62 and 64 may, for example, comprise portions of a single, type 555 integrated circuit timer.

From the multivibrators 62 and 64, the square wave pulses are fed into a discrimination circuit 66 in which coincidence of pulses from the separate multivibrators is determined, as described below. The output of the discrimination circuit 66 is fed into an integrating circuit 72 and thence to a threshold detector 74. From the detector 74, the signal is amplified by a driver 76 which drives or lights the indicator light 34, when and only when there is a signal from the first microphone 22 and no coincident signal from the second microphone 24.

Logic of the discriminator circuit 66 is illustrated in FIG. 4 which shows the four possible combinations of signals and nonsignals from the multivibrators 62 and 64, corresponding to sounds or no sounds picked up by the microphones 22 and 24. In the diagram and for purposes of discussion, a signal corresponding to a sound is identified by a digital "1"; absence of sound is identified by a digital 0. Pulses from the multivibrators 62 and 64 thus comprise either 1's or 0's. When a sound is picked up by the first microphone 22 (output of the multivibrator 62 = 1) and no coincident sound is picked up by the second microphone 24 (coincident output of the multivibrator 64 = 0)—a condition strongly indicative of a Korotkoff sound having been picked up—the output of the discriminator circuit 66, indicated by Column A in FIG. 4, is in a first preselected state, for example a 0 state, which will cause the indicator light 34 to be turned on. For all other combinations of coincident sounds (1's) and no sounds (0's), the output of the discriminator circuit 66 is in a second state, for example a 1 state, and light 34 remains unlit. Column B indicates the condition of no sound picked up by the microphone 22 (output of the multivibrator 62 = 0) and sound picked up by the microphone 24 (output of the multivibrator 64 = 1), indicative of only a background noise; thus, the output of the discriminator circuit 66 is a 1. Column C indicates sounds picked up by both microphones 22 and 24 (1's from both multivibrators 62 and 64) indicating the possibility that the sound picked up by the microphone 22 may be noise and not a Korotkoff sound; again, the discriminator circuit 66 output for such is a 1. Column D illustrates the situation in which there is no sound from either the microphone 22 or 24 (0's from both multivibrators 62 and 64); the output of the discriminator 66 remains at the 1 level.

A condition of importance remains to be examined: that condition illustrated in FIGS. 5, 5a and 5b in which there are only partially coincident 1 pulses from the multivibrators 62 and 64. Such a condition indicates that not entirely coincident sounds have been picked up by the first and second microphones 22 and 24. In the situation illustrated in FIG. 5, the 1 output of the multivibrator 62 leads the 1 output of the multivibrator 64 by a time $\tau$ (corresponding to the first microphone 22 picking up a sound a short time before the second microphone 24 picks up a sound). The output of the discrimination circuit 66 thus is caused to remain at the 1 level (coincidence of 1 signals) except for a short time $\tau$ during which it falls to a 0 level. The integrator 72 integrates the discriminator output, and if the time $\tau$ is sufficiently long (FIG. 5a) the output of the integrator 72 will reach a predetermined threshold level $V_t$ of the threshold detector 74, and the light 34 will be triggered on. If, however, the time $\tau$ is too short, the output of the integrator 72 will not reach the threshold level $V_t$, and the light 34 will not be triggered (FIG. 5b). The threshold voltage $V_t$ can easily be preselected by varying resistances and capacitances within the detector 74, and is preferably adjusted so that the light 34 will be triggered for the time $\tau$ equal to or greater than about 50 milliseconds. This assures sufficiently non-coincident signals to be indicative of the presence of a true Korotkoff sound.

As shown in FIG. 3, the discrimination circuit 66 may comprise first and second NAND gates 78 and 80. The output of the multivibrator 62 is fed into one input of the first gate 78 and the output of the multivibrator 64, which is inverted by the second gate 80, is fed into a second input of the first gate. This creates the logic illustrated in FIG. 4 and described above. Other types of circuitry may be employed in the discriminator 66, so long as the logic is preserved. It is to be understood, however, that the logic states of 1's and 0's may be reversed, the only requirement being, as above stated, that the discrimination circuit 66 have a predetermined first output level corresponding to a sound being picked up by the first microphone 22 and no coincident sound picked up by the microphone 24, and a second predetermined level for all other conditions.

In the manner described, the light 34 is triggered when true Korotkoff sounds are picked up by the first microphone 22 and at no other time. An operator need only watch the pressure indicated on the manometer 18 and the light 34 as he slowly releases pressure from the bladder 12. Systolic blood pressure is recorded when the light 34 starts flashing and diastolic pressure is recorded when the light stops flashing.

Although the output of the driver 76 has been illustrated and described as triggering an indicator light 34, the driver can be used to develop other output indications. For example, as illustrated in FIG. 6, the output of the driver 76 is used to trigger a "pneumatic memory" system. The pneumatic memory comprises a systolic pressure gauge 100 and a diastolic pressure gauge 102. Associated with the systolic gauge 100 is a normally open pressure shutoff valve 104 which is connected in series with a portion of the tube 20, through pressure lines 106 and 108, to the gauge 100. A normally closed pressure valve 110 is connected to the diastolic gauge 102 through pressure lines 112 and 114 from the tube 20. The output of the control box 28 (that is, the output of the driver 76) is fed, via an electrical line 116 to a monostable flip-flop 118, the output of which is in turn connected to the valve 104 by a line 120. The output of the control box 28 is also fed, via a line 122, to one input of an OR gate 124, the output of which is fed by a line 126 to a pulse generator 128, and thence, via a line 130, to the valve 110. A reset OR gate 134 is connected by a line 136 to the flip-flop 118 and by line 138 to a second input of the gate 124. One input 140 of the reset gate 134 may be connected to a "push-to-reset" switch 142. A second input 144 of the reset gate 134 is connected to an automatic reset pulse generator 146 (as described below).

The cuff 10 is fastened about a patient's arm and the bladder 12 is inflated to a pressure above the anticipated systolic blood pressure. The valve 104 is open and the pressure in the bladder 12 is directed to the gauge 100; the valve 110 is closed and no pressure is read on the gauge 102. Pressure is slowly released from the bladder, and a triggering output is provided by the driver 76 in the control box 28 at the first true Korotkoff sound picked up by the microphone 22, as described above. This triggering pulse causes the flip-flop 118 to change state and close the valve 104, trapping pressure, which is the systolic blood pressure, in the gauge 100. The flip-flop 118 then remains in the flipped state and the valve 104 remains closed, so that pressure of the gauge 100 need not be immediately read. However, the valve 110 is caused to open momentarily at each triggering output of the box 28, the pulse generator 128 shaping the output of the gate 124 to accomplish this. As pressure in the bladder 12 is reduced and at each successive Korotkoff sound, a lesser pressure is registered on the gauge 102. When the last triggering pulse has been provided, indicating a cessation of Korotkoff sounds, the valve 110 will remain closed and the pressure trapped in the gauge 102 will be the diastolic pressure. An operator merely reads the systolic pressure from gauge 100 and the diastolic pressure from the gauge 102. After the reading has been completed, the system may be returned to its initial condition by depressing the switch 142 or by supplying a signal from the reset generator 146.

The above-described variation is easily adaptable to an automatic inflation-deflation system permitting the systolic and diastolic pressures to be taken with the press of a single switch. A start switch 150 turns on a timer 152, preset for about 10–20 seconds, the timer turning on a small air pump 154 which inflates the bladder 12 and at the same time closing a normally open bleed valve 156 to hold the air in the bladder. At the end of the cuff inflation period, the cuff pressure will be about 30 mm of mercury above systolic pressure. When the timer 152 shuts off, the air pump 154 is stopped, the bleed valve 156 is opened and a reset pulse is applied by the generator 146 to the reset gate 134. The bleed valve 156 is metered so that the cuff pressure decreases about 3 mm of mercury per second. The operation is otherwise as described before, with the systolic pressure being displayed upon the gauge 100 and the diastolic pressure being displayed upon the gauge 102 after pressure in the bladder 12 has been released.

It is to be appreciated that the triggering output of the driver 76 may be used in still other ways to indicate when systolic and diastolic blood pressure should be read. For example, if the pressure in the bladder 12 is recorded on a recording oscillograph (not shown), the output of the driver 76 may be supplied to one channel of the recorder. After depressurizing the bladder 12, the systolic and diastolic blood pressures can be read from the recording by reference to the presence or absence of the triggering pulses.

Other means for microphone signal discrimination may also be provided. For example, FIG. 7 illustrates circuitry in which is electronically computed the ratio between the magnitudes of signals from the first and second microphones 22 and 24. Background sounds simultaneously picked up by the two microphones 22 and 24 can be expected to have about an equal magnitude — particularly if both of the microphones have pick-up portions directed inwardly toward a patient's arm—hence, the ratio of signal magnitudes in such a case will be about one. However, Korotkoff sounds picked up by the first microphone 22 over the brachial artery are expected to be greater, by a factor of about two or more, than Korotkoff sounds normally picked up by the other microphone. That is, if the ratio of simultaneous signal magnitudes (dividing the magnitude of the first microphone signal by the magnitude of the second microphone signal) is substantially greater than one, for example, about 1.4 or greater, there is strong assurance that the sound picked up by the first microphone was a true Korotkoff sound. If a sound is picked up by the first microphone 22 and none is picked up by the second microphone 24 (an indication, as described above, that a true Korotkoff sound has been picked up), the signal ratio will also be much greater than one and an indication will also be given. On the other hand, if no sound is picked up by the first microphone 22 and sound is picked up by the second microphone 24 (an indication of background noise) the ratio of signal magnitudes will be much less than one, and no indication will be given.

To this end, signals from the filters 50 and 52 are fed into a conventional ratio determining circuit 164, in which the ratio between signal magnitudes from the first and second microphones 22 and 24 is determined. The output from the circuit 164 is fed into a comparator 166 which compares the output of the circuit 164 to a predetermined ratio or level, and thence to a one-shot multivibrator 168. If the ratio is greater than the predetermined ratio (for example about 1.4), the comparator 166 causes the multivibrator 168 to light the indicator light 34.

Since it is important that the polarity of the output signal remain constant, outputs of the filters 50 and 52 are fed through diodes 172 and 174 respectively to eliminate negative output signals to the circuit 166. Ground path resistors 176 and 178 are associated, respectively, with diodes 172 and 174. Other circuits can be used to insure the positive polarity of the two signals. It is also important that the input to the circuit 164 from the filter 50 ($V_{22}$) and from the filter 52 ($V_{24}$)

never be zero, so that the circuit can calculate the ratio. Hence, very small electrical signals $-\delta 1$ and $+\delta 2$ are added, respectively, to $V_{22}$ and $V_{24}$ through resistors 180 and 182. The actual mathematical operation performed by the circuit 164 is thus $(V_{22} - \delta 1)$ divided by $(V_{24} + \delta 2)$.

Such circuitry as just described has the advantage of enabling discrimination even when simultaneous Korotkoff sounds are picked up by both microphones 22 and 24.

Additional signal discrimination may be provided by use of conventional signal pulse width discriminators (not shown) in conjunction with the frequency bandpass provided by the filters 50 and 52 to take advantage of the fact that Korotkoff sound pulses (picked up by the first microphone 22) will generally have a different pulse width than extraneous sounds (picked up by either of the two microphones). To some extent, the pulse width is determined by the band width of the filters 50 and 52, and if the band width is too low, the pulse widths may be significantly distorted and both the Korotkoff sound signals and the extraneous noise signals will have similar pulse widths. A trade-off is thus necessary between pulse width discrimination and frequency bandpass: the frequency pass band must be narrow enough to eliminate noise, but wide enough not to distort the pulse widths excessively.

Corresponding methods for measuring systolic and diastolic blood pressure either automatically or non-automatically are thereby provided. Although there have been described hereinabove specific arrangements of a noise rejecting electronic sphygmomanometer and methods for measuring blood pressure in accordance with the invention for the purpose of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the appended claims.

What is claimed is:

1. In a sphygmomanometer having a cuff, a cuff inflating bladder and a bladder pressure measuring element, where the cuff is adapted for positioning around a patient's limb, for measuring the patient's blood pressure intensity by monitoring Korotkoff sounds as bladder pressure is slowly reduced from above systolic blood pressure, the improvement comprising:
   a first acoustical pickup disposed within the cuff and positioned relative to a patient's brachial artery to pick up said Korotkoff sounds;
   a second acoustical pickup disposed within the cuff and positioned away from the brachial artery to pick up background sounds;
   transducing means associated with said pickups for producing a first electrical signal corresponding to the sounds received by the first pickup and a second electrical signal corresponding to the sounds received by the second pickup; and
   electronic logic means connected to receive the first and second signals for providing an output at a first voltage level upon a comparison of said electrical signals when and only when there is a first electrical signal corresponding to Korotkoff sounds and no second electrical signal of comparable magnitude and for providing an output at a second voltage level except when said first output signal is provided.

2. The invention as claimed in claim 1 including an indicator connected to respond to the output at said first voltage level.

3. The invention as claimed in claim 2, wherein said indicator comprises a light which is lit only when said output is in said first level.

4. The invention as claimed in claim 1, including first and second pressure gauges connected to said bladder and means for trapping pressure in said gauges, said trapping means being responsive to said output to cause pressure to be trapped in said first pressure gauge when said output is at said first level and to cause pressure to be trapped in said second pressure gauge when said logic means last supplies an output of said first level.

5. The invention as claimed in claim 4, further including means for automatically inflating and deflating said bladder.

6. The invention as claimed in claim 1, wherein said two pickups are positioned relatively adjacent to each other and within the cuff adjacent said bladder.

7. The invention as claimed in claim 1, wherein said logic means includes filtering means for filtering out said electrical signal frequencies other than those in a limited range.

8. The invention as claimed in claim 1, wherein said two pickups are disposed in said cuff at a location remote from cuff connections for inflating said bladder and for said pressure measuring element.

9. The invention as claimed in claim 1, wherein said logic means causes said output to be in said first level when and only when the actual ratio between magnitudes of sound signals received from said first pickup and sound signals received from said second pickup exceed a predetermined ratio, and to be in said second level whenever said actual ratio is below said predetermined ratio.

10. The invention as claimed in claim 9, including means for adding an incremental signal to each of said first and second signals whereby said ratio is never infinity.

11. The invention as claimed in claim 1, wherein non-sound receiving portions of said pickups are sound insulated.

12. A noise rejecting electronic sphygmamanometer which comprises:
   a. A flexible cuff adapted to be wrapped and fastened around a patient's limb,
   b. an inflatable bladder disposed within a portion of said cuff,
   c. Means for inflating and deflating said bladder, whereby blood circulation in portions of a limb about which said cuff is wrapped and fastened may be stopped and may be subsequently restored,
   d. means connected to said bladder for measuring pressure therein,
   e. first and second microphones disposed in said cuff, said first microphone having a directional pickup portion directed toward a patient's limb when said cuff is wrapped and fastened therearound, said first microphone pickup portion being adapted for positioning over a brachial artery, whereby Korotkoff blood sounds in said artery may be picked up thereby, said second microphone having a directional pickup portion directed to pick up background noises, f. electronic discriminating means for receiving electrical signals from said first and second microphones and for discriminating between the electrical means responsive to an output from the discriminating means to provide a detectable indication when and only when a sound is picked up by said first microphone pickup portion and is not picked up by the second microphone pickup portion.

13. The invention as claimed in claim 12, wherein said discriminating means includes filtering means for allowing passage of electrical signals from said first and second microphones having frequencies within a limited band range.

14. The invention as claimed in claim 13, wherein said discriminating means further includes means for determining the ratio between the magnitude of signals received from said first and second microphones, and for causing said indicating means to provide said detectable indication when and only when said determined ratio exceeds a predetermined ratio.

15. The invention as claimed in claim 14, wherein said predetermined ratio is about 1.4, whereby said indicating means provides said detectable indication only when said magnitude of said first microphone signal is about 1.4 times greater than said magnitude of said second microphone signal.

16. The invention as claimed in claim 12, wherein said discriminating means further includes means for shaping said filtered electrical signals from said first and second microphones, and means for comparing said shaped signals and for causing an output of said comparing means to be at a first predetermined level, having a detectable indication, when and only when a shaped signal from said first microphone is not coincident with a shaped signal from said second microphone, and for causing said output of said comparing means to be at a second predetermined level for other microphone signal conditions.

17. The invention as claimed in claim 16, wherein said comparing means comprises a signal inverter connected to receive said shaped signal from said second microphone and a logic gate connected to separately receive the output of said inverter and said shaped signal of said first microphone.

18. The invention as claimed in claim 16, wherein said discriminating means further includes integrating means for integrating said output of said comparing means and for causing said detectable indication only when an out-of-coincidence condition of said shaped signals from said first and second microphones exists for a predetermined time interval.

19. The invention as claimed in claim 18, wherein said predetermined time interval is about 50 milliseconds.

20. The invention as claimed in claim 12, wherein said indicating means includes systolic and diastolic pressure reading gauges connected with said bladder and means for trapping pressure in said gauges in response to said indicating means, when said cuff is attached about a patient's limb and pressure in said bladder is slowly released from above systolic blood pressure levels.

21. The invention as claimed in claim 20, wherein said trapping means includes a first valve connected to said systolic gauge and a second valve connected to said diastolic gauge, said first valve being caused to close at a first instance of Korotkoff sounds being picked up by said first microphone, said second valve being caused to open momentarily at each instance of a Korotkoff sound being picked up by said first microphone.

22. The invention as claimed in claim 20 including means for automatically inflating and deflating said bladder.

23. The invention as claimed in claim 12, wherein said first and second microphones are located remotely from connections to said bladder for said inflating and deflating means for said pressure measuring means.

24. A method of indicating when systolic and diastolic blood pressures are to be read from a pressure monitoring device connected to a cuff-type sphygmomanometer having an inflatable bladder, which comprises the steps of:

a. installing a first microphone under said bladder and in a position to be over a brachial artery to pick up Korotkoff blood sounds when said sphygmomanometer is positioned about a patient's limb, b. installing a second microphone, having a sound pickup positioned to pick up background noises, c. installing said sphygmomanometer on a patient's limb and inflating said bladder until blood flow is stopped in the patient's limb under and below said sphygmomanometer, d. releasing the pressure in said bladder slowly while monitoring the pressure therein on said pressure monitoring device, e. converting sounds picked up by said first and second microphones into electrical signals, f. comparing said electrical signals from said first and second microphones and causing a detectable indication when and only when said comparison indicates a strong probability that sounds picked up by said first microphone are Korotkoff blood sounds and not background sounds, g. reading a first pressure from said pressure monitoring device at the initial onset of said detectable indication, said first pressure being the systolic blood pressure, and h. reading a second pressure from said pressure monitoring device as pressure is further reduced in said bladder at the first cessation of said detectable indications, said second pressure being the diastolic blood pressure.

25. The method as claimed in claim 24, including the step of filtering said electrical signals from said two microphones so that only frequencies in a limited range are passed and shaped.

26. The method as claimed in claim 25, including the steps of shaping said filtered and shaped electrical signals from said first and second microphones into square wave pulses, comparing the coincidence of said square wave pulses from said first and second microphones and causing said detectable indication only when a pulse from said first microphone is not coincident with a pulse from said second microphone.

27. The method of claim 25, including the step of determining the ratio between the magnitude of filtered signals from said first microphone and the magnitude of filtered signals from said second microphone, and causing said detectable indication only when said value exceeds a predetermind ratio.

28. A method for measuring systolic and diastolic blood pressures, using a cuff tupe sphygmomanometer having an inflatable bladder, which comprises the steps of:
   a. installing a first, blood-sound microphone, having a pickup under said bladder and in a position to be over a brachial artery to pick up Korotkoff blood sounds when said sphygmomanometer is positioned about a patient's limb,
   b. installing a second noise microphone, under said bladder to pick up background noises,
   c. connecting a first pressure gauge and a first pressure shutoff valve to said bladder,
   d. connecting a second pressure gauge and a second pressure shutoff valve to said bladder,
   e. installing said sphygmomanometer about a patient's limb and inflating said bladder until blood flow in the limb under and below said sphygmomanometer is stopped,
   f. releasing the pressure from said bladder slowly,
   g. converting sounds picked up by said first and second microphones into electrical signals,
   h. causing said first valve to close, thereby trapping pressure in said first gauge, the first time an electrical signal received from said first microphone is not coincident with an electrical signal received from said second microphone,
   i. causing said second valve to momentarily open, thereby admitting pressure to said second gauge, each time an electrical signal received from said first microphone is not coincident with an electrical signal received from said second microphone, and
   j. reading, when pressure in said bladder is substantially reduced, systolic blood pressure from said first gauge and diastolic blood pressure from said second gauge.

29. A method for measuring systolic and diastolic blood pressures, using a cuff-type sphygmomanometer having an inflatable bladder, which comprises the steps of:
   a. installing a first blood-sound microphone under said bladder and in a position to be over a brachial artery to pick up Korotkoff blood sounds when said sphygmomanometer is positioned about a patient's limb,
   b. installing a second, noise microphone under said bladder to pick up background noises,
   c. connecting a first pressure gauge and a first pressure shut-off valve to said bladder,
   d. connecting a second pressure gauge and a second pressure shut-off valve to said bladder,
   e. installing said sphygmomanometer about a patient's limb and inflating said bladder until blood flow in the limb under and below said sphygmomanometer is stopped,
   f. releasing the pressure from said bladder slowly,
   g. converting sounds picked up by said first and second microphones into electrical signals,
   h. causing said first valve to close, thereby trapping pressure in said first gauge, the first time the ratio between magnitudes of electrical signals received from said first and second microphones exceeds a preselected level,
   i. causing said second valve to momentarily open, thereby admitting pressure to said second gauge, each time said ratio between magnitudes of electrical signals received from said first and second microphones exceeds said preselected level, and
   j. reading, when pressure in said bladder is substantially reduced, systolic blood pressure from said first gauge and diastolic blood pressure from said second gauge.

* * * * *